United States Patent
Eerden et al.

(10) Patent No.: US 9,248,307 B2
(45) Date of Patent: Feb. 2, 2016

(54) BILINGUAL LANGUAGE CONTROLLER FOR AN AUTOMATED EXTERNAL DEFIBRILLATOR

(71) Applicant: KONINKLIJKE PHILIPS N.V., Eindhoven (NL)

(72) Inventors: Jacco Christof Eerden, Eindhoven (NL); Alan Paul Greenstein, Seattle, WA (US)

(73) Assignee: KJONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/375,991

(22) PCT Filed: Feb. 1, 2013

(86) PCT No.: PCT/IB2013/050860
§ 371 (c)(1),
(2) Date: Jul. 31, 2014

(87) PCT Pub. No.: WO2013/114325
PCT Pub. Date: Aug. 8, 2013

(65) Prior Publication Data
US 2015/0046149 A1   Feb. 12, 2015

Related U.S. Application Data

(60) Provisional application No. 61/593,987, filed on Feb. 2, 2012.

(51) Int. Cl.
*G06F 17/20* (2006.01)
*G06F 17/27* (2006.01)
*A61N 1/39* (2006.01)
*G06F 9/44* (2006.01)
*G06F 17/28* (2006.01)

(52) U.S. Cl.
CPC ............ *A61N 1/3993* (2013.01); *G06F 9/4448* (2013.01); *G06F 17/289* (2013.01)

(58) Field of Classification Search
None
See application file for complete search history.

(56) References Cited

U.S. PATENT DOCUMENTS

| | | | | |
|---|---|---|---|---|
| 6,148,233 A * | 11/2000 | Owen | .................. | A61N 1/0452 607/5 |
| 6,154,673 A * | 11/2000 | Morgan | ............... | A61N 1/3993 607/5 |
| 6,611,708 B1 * | 8/2003 | Morgan | ............... | A61N 1/3993 607/5 |
| 7,257,440 B2 * | 8/2007 | Morgan | ............... | A61N 1/3993 607/5 |
| 7,653,435 B2 * | 1/2010 | Halsne | .................... | A61N 1/39 607/5 |
| 2003/0028219 A1 * | 2/2003 | Powers | .................... | A61N 1/39 607/5 |
| 2004/0049234 A1 * | 3/2004 | Morgan | ............... | A61N 1/3993 607/5 |
| 2004/0215246 A1 * | 10/2004 | Powers | .................... | A61N 1/39 607/5 |

(Continued)

FOREIGN PATENT DOCUMENTS

| WO | 2006016288 A1 | 2/2006 |
|---|---|---|
| WO | 2008059397 A1 | 5/2008 |

*Primary Examiner* — Marcus T Riley (57) ABSTRACT

A language controller (20) is described which can be installed on the front face of an automated external defibrillator (AED) in order to establish the language of the AED user interface. The language controller is in the form of a labeled plaque (210) which informs the user which language is currently in use. The plaque may also contain a button (222) which enables toggling from one language to another. Memory may also reside in the plaque to provide language data to the AED.

19 Claims, 4 Drawing Sheets

(56) References Cited

U.S. PATENT DOCUMENTS

| | | | | |
|---|---|---|---|---|
| 2008/0097533 A1* | 4/2008 | Halsne | ............... | A61N 1/3993 607/5 |
| 2009/0125074 A1* | 5/2009 | Ochs | ............... | A61N 1/39 607/5 |
| 2015/0005836 A1* | 1/2015 | Jonsen | ............... | A61N 1/37247 607/6 |
| 2015/0046149 A1* | 2/2015 | Eerden | ............... | A61N 1/3993 704/8 |

* cited by examiner

FIG. 6d

BILINGUAL LANGUAGE CONTROLLER FOR AN AUTOMATED EXTERNAL DEFIBRILLATOR

CROSS-REFERENCE TO PRIOR APPLICATIONS

This application is the U.S. National Phase application under 35 U.S.C. §371 of International Application No. PCT/IB2012/050860, filed on Feb. 1, 2013, which claims the benefit of U.S. Provisional Patent Application No. 61/593,987, filed on Feb. 2, 2012. These applications are hereby incorporated by reference herein.

This invention relates to an improved user interface for an automated external defibrillator (AED), and, in particular, to an AED which can be pre-configured by the owner to provide visual and aural instruction to the user in one or multiple desired languages. The invention also relates to a method for preparing the AED for operation in the desired language.

Sudden cardiac arrest ("SCA") most often occurs without warning, striking people with no history of heart problems. It is estimated that more than 1000 people per day are victims of sudden cardiac arrest in the United States alone. SCA results when the electrical component of the heart no longer functions properly, causing an abnormal sinus rhythm. One such abnormal sinus rhythm known as ventricular fibrillation ("VF") is caused by abnormal and very fast electrical activity in the heart. As a result, the heart fails to adequately pump blood through the body. VF may be treated by applying an electric shock to a patient's heart through the use of a defibrillator. Defibrillators include manual defibrillators, automatic or semi-automatic external defibrillators ("AEDs"), defibrillator/monitor combinations, advisory defibrillators and defibrillator trainers. The shock from the defibrillator clears the heart of abnormal electrical activity (in a process called "defibrillation") by producing a momentary asystole and an opportunity for the heart's natural pacemaker areas to restore normal rhythmic function. However, quick response after the onset of VF is critical because there is an increased likelihood that a patient will not be resuscitated or will suffer irreversible brain damage when the heart has not been pumping blood for more than 5 minutes.

Over the last several years defibrillators have become more portable and have begun moving into the hands of individuals who initially make contact with a person suffering from VF but have little or no formal medical training. As a result, equipment that was once available only in the hospital environment and operated by medically trained personnel is now being used in non-hospital environments by police officers, flight attendants and security guards, to name a few, as part of a first-line action in the administration of first aid. The benefit of making this equipment available is that it is more likely that a victim of SCA will receive the life-saving shock within the first few critical minutes of VF. Of course, with little or no medical training, the individuals who first make contact with a patient need to be instructed on the use of the defibrillator to deliver shock therapy. These defibrillators are often designed to operate nearly automatically and with little user intervention, often providing voice and text prompts to a medically untrained user on the operation of the defibrillator. Providing voice and text prompts for a user on the operation of a defibrillator reduces the amount of time necessary for the user to review protocols prior to deploying the defibrillator. Thus, a medically untrained individual first on the scene can nevertheless administer therapeutic shock to a patient in a short time.

As previously discussed, currently available external defibrillators often convey instructions, status information or other information to assist the defibrillator operator on the operation of the defibrillator. Some external defibrillators announce such information audibly through a speaker, either in addition to displaying information or instead of displaying information.

In areas where more than one language is commonly spoken, and not necessarily with equal proficiency, there is a need to have a defibrillator that adapts the language of the prompts in response to the user's indication of language proficiency. This need is especially acute for defibrillators which are deployed in public areas, where there is no prior knowledge of which language a rescuer might speak. There are a number of locales where the need for a multilingual defibrillator is especially acute. The southern United States, for example, has a large number of people who speak exclusively English or exclusively Spanish. French Canada also has a population which may speak exclusively English or exclusively French. In Europe, many European languages coexist in a small area, increasing the likelihood of a rescuer who speaks a different language than the language set up on the defibrillator.

As a result, external defibrillators have been developed that can provide audible instructions and information on the operation of the defibrillator in different languages. These defibrillators are pre-programmed with audible instructions for more than one language from which audible instructions for one language are selected. Selection of the language in which the audible instructions and information are provided is typically made through button controls on the front panel of the defibrillator or through user responses to defibrillator prompts that are made during the operation of the defibrillator.

Although audible instructions on the operation of a defibrillator are available for different languages, the selection process for choosing which one of the languages to receive audible instructions can be distracting to a user, and also takes time to do. During a high stress rescue, any additional time or attention away from the task of applying rapid defibrillation to a patient only reduces the chance of success. Moreover, since the audible instructions are provided in only one language by the defibrillator, several rescuers having fluency in different languages will not be able to both benefit from the audible instructions provided by the defibrillator during administration of the therapy, thus precluding receipt of assistance from one or the other individual. Therefore, there is a need for a multilingual defibrillator providing audible instructions in more than one language during its operation.

In addition, the manufacture of AEDs must serve the needs of customers in a large number of countries. The current practice for manufacturing AEDs is to create a baseline AED using a default language stored in internal read-only memory. If a non-default language is needed by the customer, the baseline AED must be loaded with that language at the factory. No opportunity for changing languages in the field is possible. Considerable complication and expense is introduced into the manufacturing and distribution system to track and maintain AEDs in various languages. There is therefore a need for a more efficient method of providing a defibrillator which can be configured into different languages by, for example, the distributor or the end user.

The present invention is directed to a portable medical device, as exemplified by an AED, which can be configured by the end user to provide operating instructions in one of several languages. The configuration is enabled by a labeled language controller which is installed on the front face of the AED. The language controller includes an encoded controlling element which uniquely identifies an audible language to be used by the AED. When the language controller is joined to the AED, the AED senses the controlling element and automatically configures itself to provide audible instructions in the identified language. In addition to configuring the AED, the language controller ensures that the AED language labeling matches its behavior. The same language controller that controls language also marks the AED with that language.

It is thus one object of the present invention to provide a portable medical device which is field-configurable to change the user language. The device includes a memory having stored therein data files representative of audible prompts in a plurality of languages, a controller coupled to the memory and configured to operate the portable medical device in one of the languages, a sensing element for selecting one of the languages and a portable medical device case housing which includes the sensing element and a mount for a language controller. The invention further includes a language controller which can be mounted on the portable medical device mount, the language controller being labeled to indicate the particular language. The language controller has a controlling element which identifies the placard language and conveys the identification to the portable medical device via the sensing element. The features operate together to cause the portable medical device to configure itself to generate user prompts in the identified language when the language controller is installed. The invention may optionally include a button on the language controller which, when pressed, toggles the medical device to operate in a second language.

It is another object of the invention to provide a language controller for an AED. The language controller includes a plaque which is labeled to indicate a language, a controlling element to identify the language to an AED, and a securing mechanism to mount the language controller onto the front face of an AED.

It is another object of the invention to provide a language controller having a button which, when pressed, toggles the AED on which it is mounted to begin operating in a second language. The language of operation may be stored within the AED or in a memory in the language controller itself.

It is a further object of the invention to provide a method for configuring the operating language of an AED by the end user. The method includes the steps of providing an AED and a labeled language controller, mounting the language controller onto the AED, sensing at the AED the language of the language controller, and automatically operating the AED with user prompts in that language. The method may also include a step of toggling the language by use of a button provided on the language controller.

Figure 1:
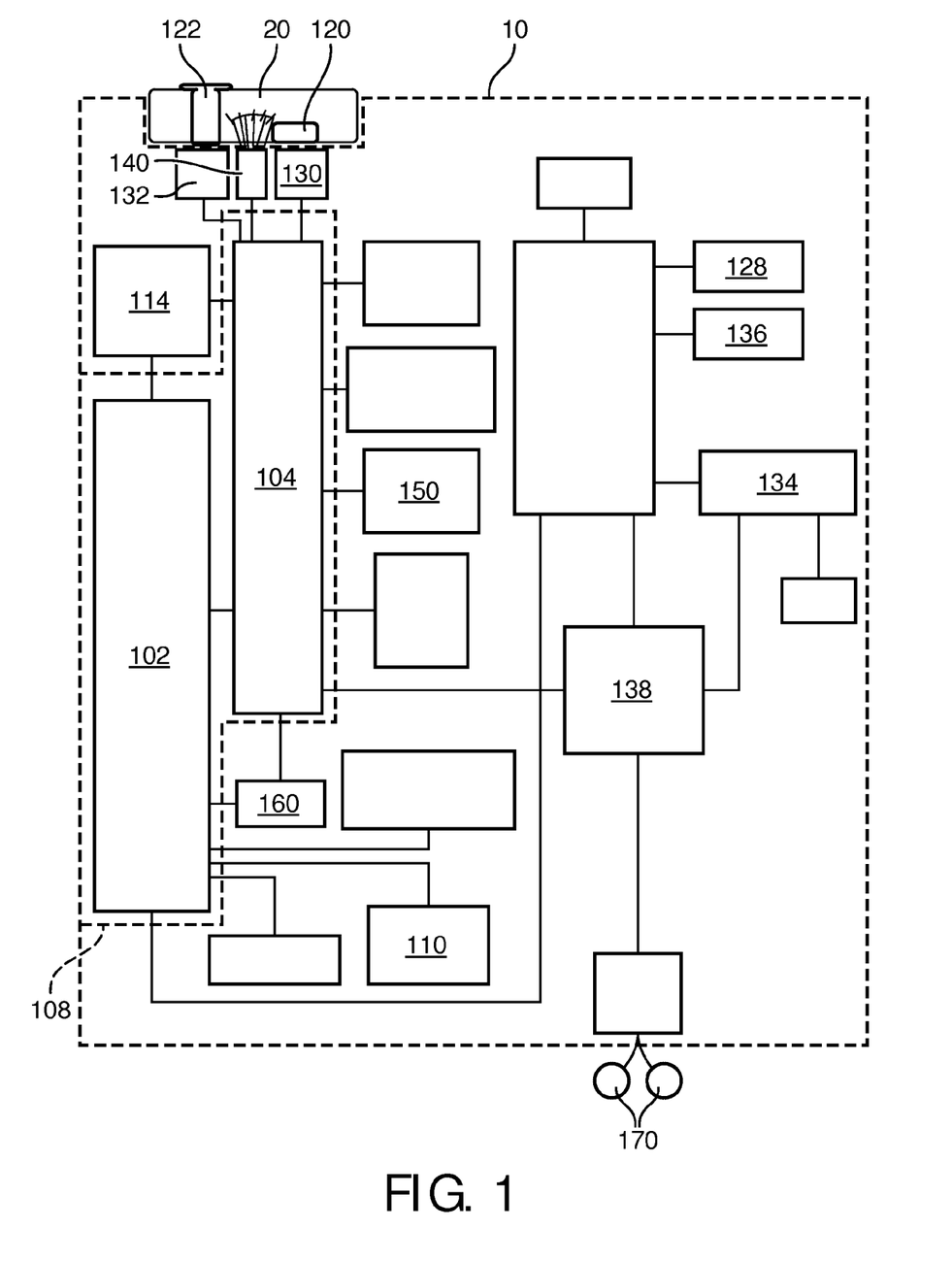
FIG. 1 is a functional block diagram of a portable medical device, here exemplified by an automated external defibrillator (AED), in which embodiments of the present invention can be implemented.

FIG. 1 is a block diagram of a multiple language portable medical device 10, in this example an AED, connected with a language controller 20 according to an embodiment of the present invention. FIG. 1 illustrates some conventional features of AED 10, including an energy source 138 which provides therapeutic voltage or current pulses to a pair of electrodes 170. Electrodes 170, disposed to be electrically attached to a patient (not shown), may also detect and monitor the patient's electrical heart rhythm for use in determining whether therapy is necessary. A battery 134 provides power to the AED 10. Status interface 128 provides a visual or aural indication of the readiness of the AED 10, such as with a blinking light, graphical indicator, or beeper.

The AED 10 is activated by the user, such as with on/off switch 136, or by sensing the opening of the AED housing with case opening sensor 110. A speaker 150 provides aural instructions, for example during a cardiac rescue, which guide the user through the appropriate steps of defibrillation and/or cardiopulmonary resuscitation. If a defibrillating shock is necessary, the user is guided to deliver the shock by pressing a shock button 160.

Control functions of the AED 10 may be divided among a main processing unit (MPU) 102 and a gate array 104. For example, MPU 102 may control the functions of the shock button 160, while gate array 304 controls speaker 150. Many variations of the controlling architecture within AED 10 are possible, and fall within the scope of the contemplated invention. All components which serve to manage the conventional functions of the AED 10 will be referred to as controller 108.

FIG. 1 also shows the features in AED 10 which enable use in a multiplicity of languages. Controller 108 accesses a read-only memory 114, which stores data relating to a plurality of languages. The appropriate language data may be used by controller 108 to generate audible prompts to the user via speaker 150. Controller 108 is preferably disposed to sense the progress of the procedure, and issue audible and/or visual prompts appropriate to that portion of the procedure.

Still referring to FIG. 1, a language controller 20 is shown in connection with AED 10. As will be further described, language controller 20 pertains to a particular language, and enables the connected AED 10 to operate in that language. The language controller 10 is labeled such that it is clear to the user as to which language the AED 10 will operate.

The language controller 20 includes an integrated controlling element 120. The controlling element 120 provides a unique signal which identifies the language represented by the language controller 20. For example, if language controller 20 is intended to enable instructions in German, controlling element 120 is so encoded.

AED 10 includes a sensing element 130 which is disposed to sense the controlling element 120 signal when the language controller 20 is mounted to AED 10. When sensing element 130 senses the encoded identifier signal from controlling element 120, the signal is passed to controller 108. Controller 108 responds to the signal by accessing the corresponding language data from memory 114, and thereafter using that data to issue audible and verbal instructions to the user via speaker 150.

The particular means of communicating between controlling element 120 and corresponding sensing element 130 may be of any technology currently known in the art. In particular, the communication may be by active or passive optical sensing, by radio frequency identification, electromagnetic sensors, or through magnetic effects such as Hall Effect sensors. Communication may also be by direct electrical contact between pins on one element and encoded circuitry on the other element, or by mechanical key and sensing switch-type mechanisms.

In an alternate embodiment, communication between language controller 20 and AED 10 may also include language program data which is stored on the language controller 20. In this embodiment, language controller 20 includes its own language read-only memory, which is conveyed via a communication port 524 in the controlling element/sensing element path to memory in AED 10. Thus, controller 108 may be disposed to operate with language data directly from the language controller 20 or from the AED memory.

The interaction between controlling element 120 and sensing element 130 upon installing the language controller 20 into AED 10 is all that is needed to shift the language operating mode of the AED 10. FIG. 1 illustrates, however, an additional embodiment which includes a language button 122 on language controller 20. Language button 122 is disposed to interact with a language switch 132 on the AED 10. Controller 108 senses a button press via switch 132 and immediately switches the AED 10 operation to operate in the particular language of the language controller. Controller 108 may also toggle the AED 10 language operation back to the original language upon sensing a subsequent press of the button 122. Thus, this embodiment enables a bilingual mode of operation in AED 10.

Figure 5:
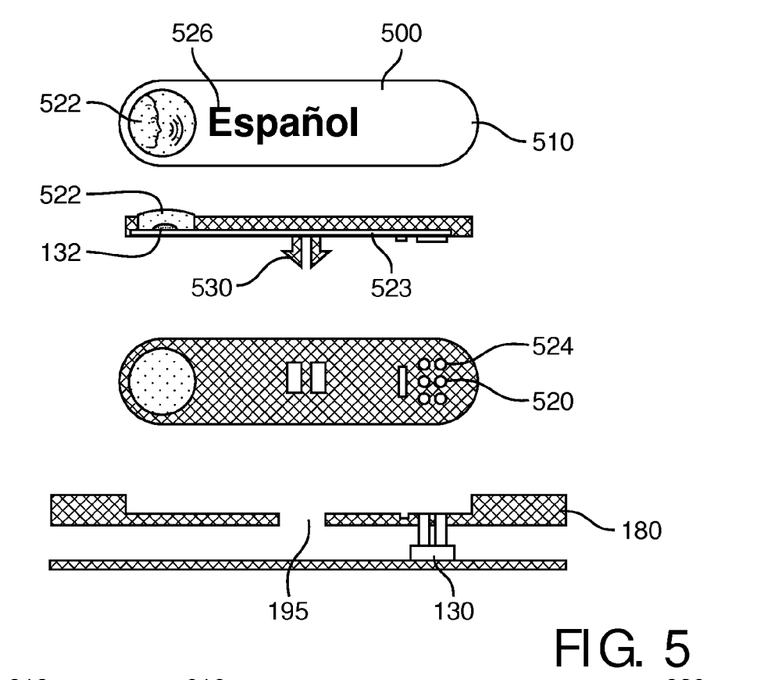
FIG. 5 illustrates several views of a language controller according to another embodiment of the present invention, showing the components and respective components on an AED.
Figure 6A:
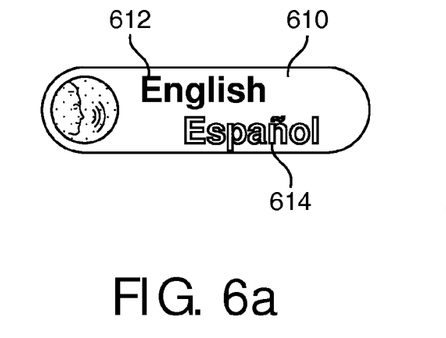
FIG. 6 illustrates several arrangements of a language controller according to another embodiment of the present invention, showing labels, buttons, and lighted indications on the language controller.
Figure 6B:
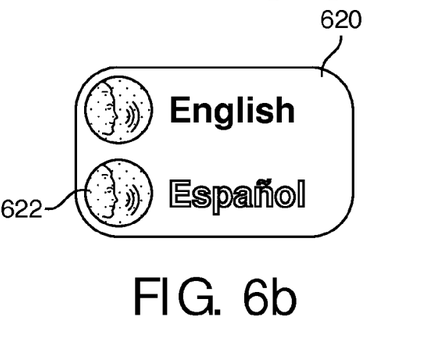
Figure 6C:
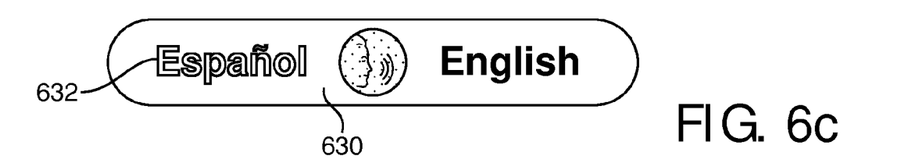
Figure 6D:
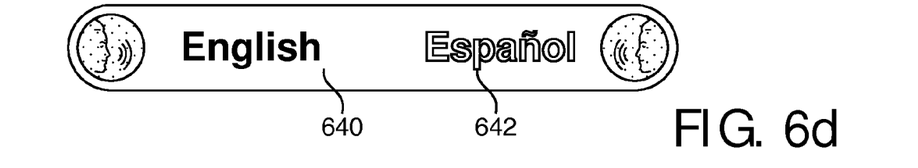

Referring to FIG. 5, language switch 132 may alternatively be disposed within a language controller 500 instead of within AED 10. The operation of the button would thus be conveyed to AED 10 via a circuit trace 523 and communication port 524 or by equivalent dedicated switch contacts.

FIG. 1 further illustrates an optional backlight 140 which illuminates the particular mode of language operation through labeling disposed on the face of language controller 20. Controller 108 may activate backlight 140 when the AED 10 is activated or when the optional language button 122 is pressed. In this embodiment, the language controller 20 has translucent areas under the language controller label through which the backlight 140 shines. A second backlight 141, as shown in FIG. 2, may be included in those embodiments which allow toggling between two languages.

The portable medical device which interoperates with a language controller may be other than an AED 10. One example is a manual defibrillator. Another example is a defibrillator trainer that simulates the behavior of a manual or automatic/semi-automatic defibrillator in use, in which case the energy source 138 may be omitted. The invention may also be disposed on non-defibrillating portable medical devices, such as handheld diagnostic ultrasound machines, blood pressure monitors and the like.

Figure 2A:
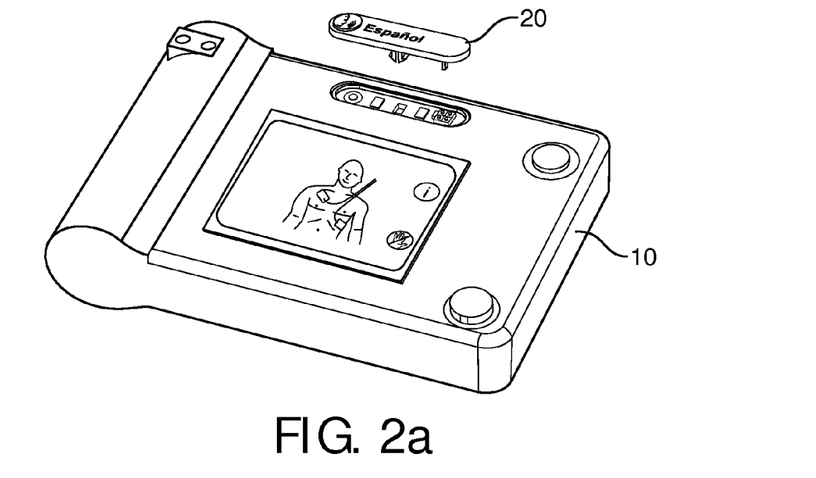
FIG. 2*a* is an isometric view of am AED and a language controller according to an embodiment of the present invention.

FIG. 2a is an isometric view of an AED 10 and a language controller 20 according to a preferred embodiment of the present invention. As can be seen there, language controller 20 is disposed as a labeled plaque which is fitted into a corresponding mount on AED 10. The illustrated embodiment shows that, to prepare the AED 10 for use in a desired language, the user first obtains a language controller 20 which is here encoded to identify the language as Spanish. The user installs the language controller 20 into the AED 10 mount, here via a snap connection. The AED 10 then senses the presence and identity of the language controller 20 and reconfigures itself to operate in the language of the controller. If a language button is provided on the language controller 20, a press of the button is sensed by AED 10 which then toggles itself to begin operating in the language of the controller. The language label provided on the language controller 20 is optionally illuminated by AED 10 when operating in that language.

FIG. 2a also illustrates a preferred embodiment that once the language controller 20 is installed flush to the front face of AED 10, there is no further feature to allow its removal in the field. This is preferred because the inventors have discovered that the reliability of AED 10 may be compromised if the plaque is removable, a missing plaque may permit water and debris to enter the AED 10 case via the mount, and that offering a user the option of swapping out plaques during a rescue introduces unacceptable delay and confusion into the rescue. It is instead preferred that the plaque removal be permitted only during non-emergency maintenance and service periods.

FIG. 2a also shows that a "blank" language controller could optionally be provided which contains no control features at all. The blank language controller would instead operate to merely fill and seal the AED 10 mount area, and cover the underlying sensing features. Controller 108, detecting the lack of the controlling element, would configure the portable medical device to operate in a default language installed within the device. Thus, it can be seen that the AED 10 could be manufactured as a universal language device, and be shipped in a single configuration. Subsequent installation of the language controller 20 by the distributor or end user enables the AED 10 to be mass-customized in the field. The invention thus reduces manufacturing complexity and cost.

Similarly, if controller 108 detects the presence of the controlling element, but also detects an error, controller 108 would configure the portable medical device to operate in the default language. This feature maximizes the reliability of operation during an emergency situation.

Figure 2B:
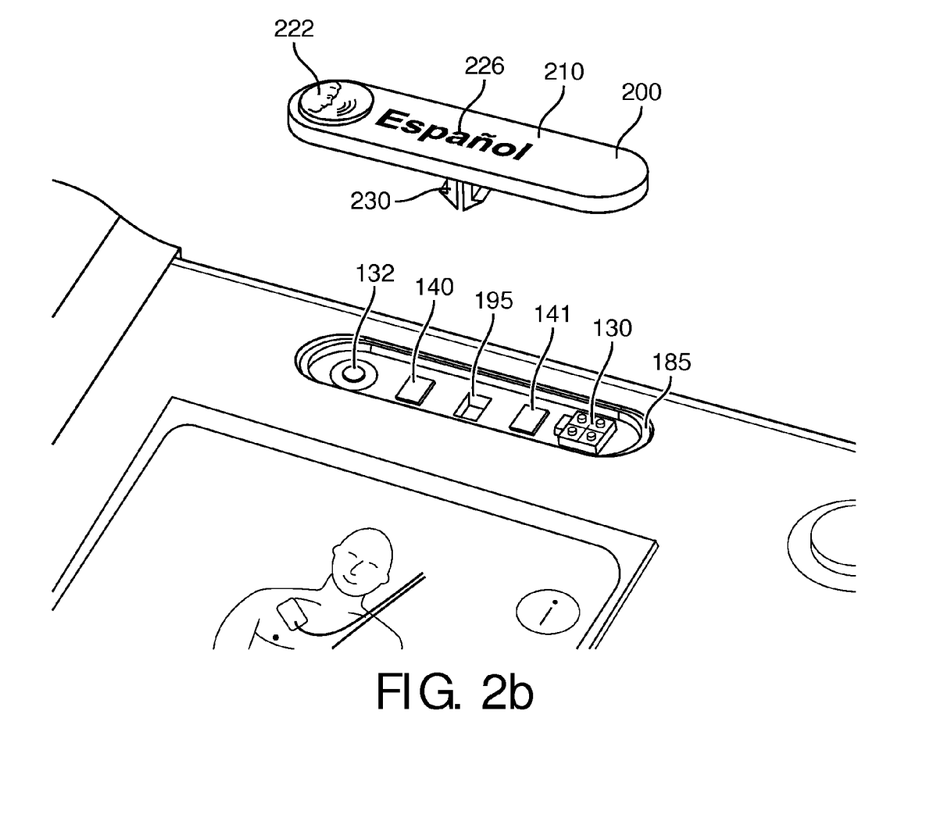
FIG. 2*b* is a close-up view of the language controller features and corresponding features on the AED, according to an embodiment of the present invention.

FIG. 2b is a more detailed isometric view of the language controller features and corresponding features on the AED, according to the preferred embodiment of the present invention. Language controller 200 is shown comprised of a plaque 210 having a snap connector 230, which is snapped into the AED mount at connector slot 195. The language controller 200 is labeled with a language indicator 226. Preferably, the plaque is constructed of a polymeric material which is durable and relatively rigid. The plaque 210 portion which underlies language indicator 226 is preferably of a translucent material such that backlight 140 and/or 141 can illuminate the indicator 226. When installed together, the front surfaces of language controller 200 and AED case 180 should be flush or nearly flush. A surface comprising a moisture-proof seal 185 is preferably disposed around the engagement periphery of plaque and mount in order to prevent liquid and debris from entering the AED or under-plaque regions.

Figure 3:
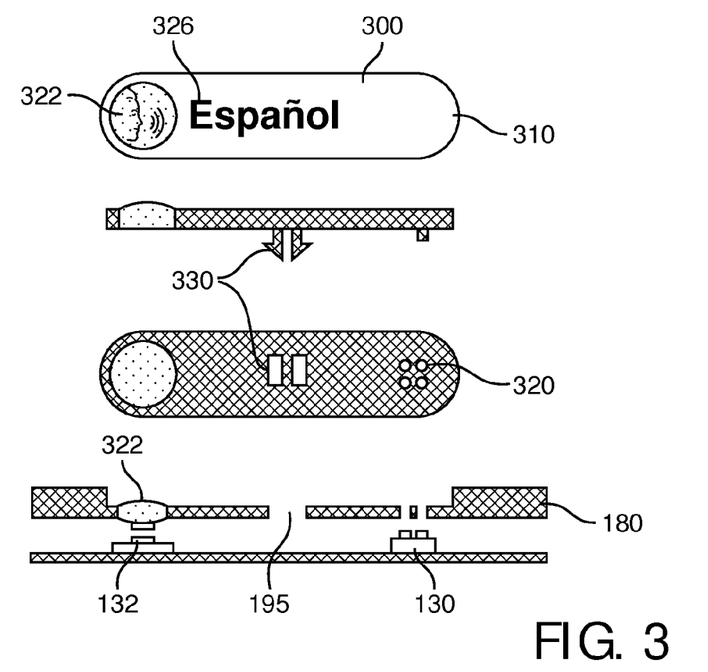
FIG. 3*a* illustrates several views of a language controller according to another embodiment of the present invention, showing the components and respective components on an AED.
FIG. 3*b* illustrates several views of a language controller according to another embodiment of the present invention, showing the components and respective components on an AED.
Figure 4:
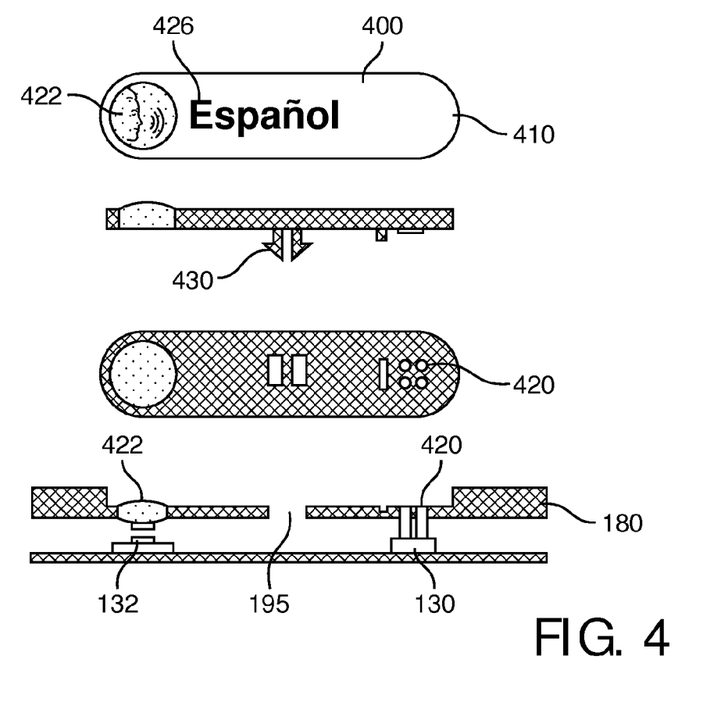
FIG. 4 illustrates several views of a language controller according to another embodiment of the present invention, showing the components and respective components on an AED.

If optional language button 222 is provided, various means known in the art may be employed to allow the plaque 210 to rotate or flex slightly upon the press of button 222, in order to operate the underlying switch 132. Preferably, language button 222 is a membrane button having a compressible polymeric material less rigid than that of the plaque 210. The membrane material is disposed through the thickness of the plaque 210 such that a user press can operate underlying switch 132 without undue flexure of the plaque. FIGS. 3b and 4 illustrate a cross section view of a membrane button 322, 422.

FIG. 2b also illustrates the disposition of sensing element 130. In this embodiment, sensing element 130 is a set of program pins which contact corresponding conductive areas disposed on controlling element 220 on the AED-facing side of language controller 200. The controlling element 220 is encoded with the identity of the language of controller 200, here shown as Spanish.

FIG. 3a illustrates several views of a language controller 300 according to another embodiment of the present invention, showing a language controller 300 comprised of a plaque 310. Snap connector 330 engages language controller 300 to the AED case 180 at connector slot 195. This embodiment includes no language button on the language controller 300, Instead, sensing element 130 is communicatively connected to controlling element 320 when the language controller 300 is installed to cause the AED to reconfigure. The connection identifies to the AED the particular language of the controller. During operation, the AED will illuminate the language indicator 326. It can be seen from FIG. 3a that this language configuration will remain in the AED until the language controller 300 is removed, for example, at a service center or by an administrator. This relieves the user of unnecessary manipulative steps, especially during a rescue.

FIG. 3b illustrates several views of a language controller 300 according to another embodiment of the present invention, showing a language controller 300 comprised of a plaque 310. Snap connector 330 engages language controller 300 to the AED case 180 at connector slot 195 such that button 322 overlies switch 132.

In this embodiment, sensing element 130 is communicatively connected to controlling element 320 when the language controller 300 is installed. The connection identifies to the AED the particular language of the controller. During operation, the AED will illuminate the language indicator 326 whenever that language is active, for example, in response to pressing button 322.

FIG. 4 illustrates several views of a language controller 400 according to another embodiment of the present invention, showing a language controller 400 comprised of a plaque 410. Snap connector 430 engages language controller 400 to the AED case 180 at connector slot 195 such that button 422 overlies switch 132.

In this embodiment, pins on sensing element 130 physically contact corresponding conductive areas on controlling element 420 when the language controller 400 is installed. The contact arrangement identifies to the AED the particular language of the controller. During operation, the AED will illuminate the language indicator 426 whenever that language is active.

FIG. 5 illustrates several views of a language controller 500 according to yet another embodiment of the present invention, showing a language controller 500 comprised of a plaque 510. Snap connector 530 engages language controller 500 to the AED case 180. In this embodiment, language switch 132 is integrated into the language controller 500 and underlying button 522. Button operation is conveyed to the AED via a circuit trace 523 and communications port 524. Operationally, a press of button 522 toggles the language similarly to the toggling enabled by the afore-described embodiments.

Like the FIG. 4 embodiment, pins on sensing element 130 physically contact corresponding conductive areas on controlling element 520 when the language controller 500 is installed. The contact arrangement identifies to the AED the particular language of the controller. During operation, the AED will illuminate the language indicator 526 whenever that language is active.

FIG. 6 illustrates several arrangements of language controllers according to yet more embodiments of the present invention. Various arrangements of labels, buttons, and lighted indications on language controllers 610, 620, 630, 640 are shown. In particular, each language controller comprises a first language visual indicator 612 and a second language indicator 614, 622, 632, 642 respectively. In each embodiment, separate backlights on the AED are employed to illuminate the currently configured language during operation. The embodiments of FIGS. 6b and 6d also include a distinct language button for each available language. Toggling is thus not required, which may reduce confusion as to which language is selected. The second language button also enables embodiments using three languages, i.e. the default language, the first controller language and the second controller language.

Variations to the aforedescribed apparatus and method are considered to fall within the scope of the claimed invention. For example, the particular physical arrangement of the plaque with respect to the portable medical device, the particular appearance of the visual language indicator, and the relative placement of the controlling elements and sensing elements may be modified within the scope of the invention.

| Table of Elements | |
|---|---|
| Element | Name |
| 10 | Portable medical device/Automated external defibrillator (AED) |
| 20 | Language controller |
| 102 | Main Processing Unit |
| 104 | Gate Array |
| 108 | Controller |
| 110 | Case opening sensor |
| 114 | Memory |
| 120 | Controlling element |
| 122 | Language button |
| 128 | status interface |
| 130 | Sensing element |
| 132 | Language switch |
| 136 | on/off switch |
| 134 | battery |
| 138 | Energy source |
| 140 | Backlight |
| 141 | second backlight |
| 150 | Speaker |
| 160 | shock button |
| 170 | electrodes |
| 180 | AED case |
| 185 | Moisture-proof seal |
| 190 | Language controller mount |
| 192 | Language controller securing mechanism |
| 195 | Connector slot |
| 200 | language controller |
| 210 | plaque |
| 220 | Controlling element |
| 222 | Language button |
| 226 | Language indicator |
| 230 | Snap connector |
| 300 | language controller |
| 310 | plaque |
| 320 | Controlling element |
| 322 | Language button |
| 326 | Language indicator |
| 330 | Snap connector |
| 400 | language controller |
| 410 | plaque |
| 420 | Controlling element |
| 422 | Language button |
| 426 | Language indicator |
| 430 | Snap connector |

-continued

Table of Elements

| Element | Name |
|---|---|
| 500 | language controller |
| 510 | plaque |
| 520 | Controlling element |
| 522 | Language button |
| 523 | Language controller circuit trace |
| 524 | Communications port |
| 526 | Language indicator |
| 530 | Snap connector |
| 610 | One button bilingual language controller |
| 612 | visual language indicator |
| 614 | second visual language indicator |
| 620 | Two button bilingual language controller |
| 622 | Second language button |
| 630 | One button bilingual language controller |
| 632 | Second language button |
| 640 | Two button trilingual language controller |
| 642 | Second language button |

The invention claimed is:

1. A portable medical device configurable to operate in multiple languages comprising:
    a controller;
    a memory disposed in electrical communication with the controller, the memory comprising data relating to user instructions in a plurality of languages;
    a case which houses the controller and memory and comprises a mount disposed on the front face of the case;
    a sensing element disposed adjacent the mount and in electrical communication with the controller; and
    a language controller comprising
        a plaque having a visible language indicator of a first language and disposed to be secured in the mount;
        a controlling element disposed on the plaque such that the sensing element senses the controlling element when the plaque is secured in the mount,
    wherein the controller configures the portable medical device to operate in a first language of the plurality of languages based on the sensing element sensing the controlling element.

2. The portable medical device of claim 1, wherein the portable medical device comprises an automated external defibrillator.

3. The portable medical device of claim 1, further comprising:
    a translucent surface on which the visible user indicia is disposed; and
    a backlight disposed on the mount, wherein the controller illuminates the visible user indicia through the translucent surface.

4. The portable medical device of claim 1, further comprising:
    a language select button disposed on the plaque; and
    a switch disposed on the mount and under the button, the switch in electrical communication with the controller,
    wherein the controller configures the portable medical device to operate in a second language of the plurality of languages based on the switch sensing a button press.

5. The portable medical device of claim 4, wherein the button is a membrane button.

6. The portable medical device of claim 4, further comprising:
    a first translucent surface on which the visible language indicator of a first language is disposed;
    a backlight disposed on the mount and operable to illuminate the first translucent surface;
    a second translucent surface on which a second visible language indicator of a second language is disposed; and
    a second backlight disposed on the mount and operable to illuminate the second translucent surface,
    wherein the controller is operable to selectively illuminate either the first or second backlight based upon the switch sensing a button press.

7. The portable medical device of claim 1, wherein the controller configures the portable medical device to operate in a default language based on a lack of the sensing element sensing the controlling element.

8. The portable medical device of claim 1, wherein the sensing element and controlling element are selected from one of the group of optical, radio frequency identification (RFID), electrical, electromagnetic, Hall Effect sensor or mechanical contact elements.

9. The portable medical device of claim 1, wherein the controller configures the portable medical device to operate in a default language based on a detected error in the sensing element sensing the controlling element.

10. The portable medical device of claim 1 further comprising:
    a snap connector disposed on the plaque; and
    a connector slot disposed adjacent the mount,
    wherein the plaque is irremovably connected to the mount by the engagement of the snap connector to the connector slot.

11. The portable medical device of claim 1, further comprising a moisture-proof seal disposed around an engagement periphery between the plaque and the mount.

12. A language controller disposed to be mounted to an automated external defibrillator, comprising:
    a plaque;
    a visual language indicator of a language;
    a controlling element having a unique identifier of the language; and
    a securing mechanism operable to mount the language controller onto a front face of the automated external defibrillator.

13. The bilingual language controller of claim 12, further comprising:
    a memory disposed in the plaque and comprising data relating to user instructions in a plurality of languages; and
    a communications port operable to output the data to the automated external defibrillator.

14. The bilingual language controller of claim 13, further comprising a language button operable to generate a signal to the automated external defibrillator via the communications port.

15. The bilingual language controller of claim 13, further comprising:
    a language button operable to generate a signal to the automated external defibrillator.

16. The bilingual language controller of claim 12, wherein the plaque comprises a translucent portion over which the visual language indicator of a language is disposed.

17. A method for changing the user interface language in an automated external defibrillator comprising the steps of
    providing an automated external defibrillator having a mount for a language controller;
    providing a language controller encoded to identify a first language in a plurality of languages;
    installing the language controller into the mount;

sensing at the automated external defibrillator the identity of the first language; and configuring the automated external defibrillator to operate in the first language.

18. The method of claim 17, further comprising the steps of:

providing a language button on the language controller;

pressing the language button;

sensing the pressing step at the automated external defibrillator; and switching the automated external defibrillator to operate in the first language based on the sensing step.

19. The method of claim 18, further comprising the step of illuminating a language indicator on the language controller corresponding to the first language.

* * * * *